United States Patent
Shim et al.

(10) Patent No.: US 7,507,204 B2
(45) Date of Patent: Mar. 24, 2009

(54) APPARATUS AND METHOD FOR FORMING 3D ULTRASOUND IMAGE

(75) Inventors: Jaeyoon Shim, Seoul (KR); Byoung Joo Kwak, Seoul (KR); Nam Chul Kim, Daegu (KR); Sang Hyun Kim, Yangsan-si (KR)

(73) Assignee: Medison Co., Ltd., Hongchun-gun (KR)

( * ) Notice: Subject to any disclaimer, the term of this patent is extended or adjusted under 35 U.S.C. 154(b) by 485 days.

(21) Appl. No.: 11/028,042

(22) Filed: Jan. 4, 2005

(65) Prior Publication Data
US 2005/0240104 A1 Oct. 27, 2005

(30) Foreign Application Priority Data
Apr. 1, 2004 (KR) .................. 10-2004-0022567

(51) Int. Cl.
*A61B 6/00* (2006.01)
*G06K 9/00* (2006.01)

(52) U.S. Cl. .................. 600/443; 128/916; 382/169; 382/170; 382/171

(58) Field of Classification Search .............. 600/443; 128/916; 382/164, 169–171
See application file for complete search history.

(56) References Cited

U.S. PATENT DOCUMENTS

| | | | | |
|---|---|---|---|---|
| 5,457,754 A * | 10/1995 | Han et al. | ............. | 382/128 |
| 5,871,019 A * | 2/1999 | Belohlavek | ............. | 600/450 |
| 6,193,660 B1 | 2/2001 | Jackson et al. | | |
| 6,251,072 B1 * | 6/2001 | Ladak et al. | ............. | 600/443 |
| 6,375,616 B1 * | 4/2002 | Soferman et al. | ............. | 600/443 |
| 6,385,332 B1 * | 5/2002 | Zahalka et al. | ............. | 382/128 |
| 6,413,217 B1 * | 7/2002 | Mo | ............. | 600/440 |
| 6,464,642 B1 * | 10/2002 | Kawagishi | ............. | 600/454 |
| 6,575,907 B1 * | 6/2003 | Soferman et al. | ............. | 600/438 |
| 6,724,938 B1 * | 4/2004 | Matsumura | ............. | 382/199 |
| 6,778,690 B1 * | 8/2004 | Ladak et al. | ............. | 382/131 |
| 6,939,301 B2 * | 9/2005 | Abdelhak | ............. | 600/437 |
| 6,945,938 B2 * | 9/2005 | Grunwald | ............. | 600/443 |
| 6,970,587 B1 * | 11/2005 | Rogers | ............. | 382/132 |
| 7,110,583 B2 * | 9/2006 | Yamauchi | ............. | 382/128 |
| 7,162,065 B2 * | 1/2007 | Ladak et al. | ............. | 382/131 |
| 2002/0009224 A1 * | 1/2002 | Gatti et al. | ............. | 382/154 |
| 2003/0103665 A1 * | 6/2003 | Uppaluri et al. | ............. | 382/131 |
| 2003/0161513 A1 * | 8/2003 | Drukker et al. | ............. | 382/128 |
| 2004/0095477 A1 * | 5/2004 | Maki et al. | ............. | 348/222.1 |
| 2004/0151356 A1 * | 8/2004 | Li et al. | ............. | 382/131 |

(Continued)

FOREIGN PATENT DOCUMENTS

EP 1 083 443 A2 3/2001

(Continued)

*Primary Examiner*—Eric F Winakur
*Assistant Examiner*—Helene Bor
(74) *Attorney, Agent, or Firm*—Oblon, Spivak, McClelland, Maier & Neustadt, P.C.

(57) ABSTRACT

The present invention relates to a 3D ultrasound diagnostic forming a 3D ultrasound image only with volume data exiting within contour by automatically detecting the contour of a target object, comprising: a first unit for generating a region of interest (ROI) box on a 2D ultrasound image; a second unit for detecting a contour of a target object in the ROI box; and a third unit for forming a 3D ultrasound image by rendering volume data existing in the detected contour.

12 Claims, 9 Drawing Sheets

U.S. PATENT DOCUMENTS

| | | | |
|---|---|---|---|
| 2004/0193053 A1* | 9/2004 | Kato | 600/440 |
| 2004/0252870 A1* | 12/2004 | Reeves et al. | 382/128 |
| 2005/0008205 A1* | 1/2005 | Kiraly et al. | 382/128 |
| 2005/0010106 A1* | 1/2005 | Lang et al. | 600/425 |
| 2005/0063611 A1* | 3/2005 | Toki et al. | 382/299 |
| 2005/0101863 A1* | 5/2005 | Kawagishi et al. | 600/443 |
| 2005/0101864 A1* | 5/2005 | Zheng et al. | 600/443 |
| 2005/0135664 A1* | 6/2005 | Kaufhold et al. | 382/131 |
| 2005/0228250 A1* | 10/2005 | Bitter et al. | 600/407 |
| 2005/0267365 A1* | 12/2005 | Sokulin et al. | 600/437 |
| 2006/0002631 A1* | 1/2006 | Fu et al. | 382/294 |
| 2006/0197780 A1* | 9/2006 | Watkins et al. | 345/620 |
| 2007/0016019 A1* | 1/2007 | Salgo | 600/437 |
| 2007/0016048 A1* | 1/2007 | Baba et al. | 600/447 |

FOREIGN PATENT DOCUMENTS

| | | |
|---|---|---|
| EP | 1 323 380 A2 | 7/2003 |
| JP | 2000-300562 | 10/2000 |
| JP | 2002-125971 | 5/2002 |
| KR | 10-2001-0026857 | 4/2001 |
| WO | WO 00/32106 | 8/2000 |

* cited by examiner

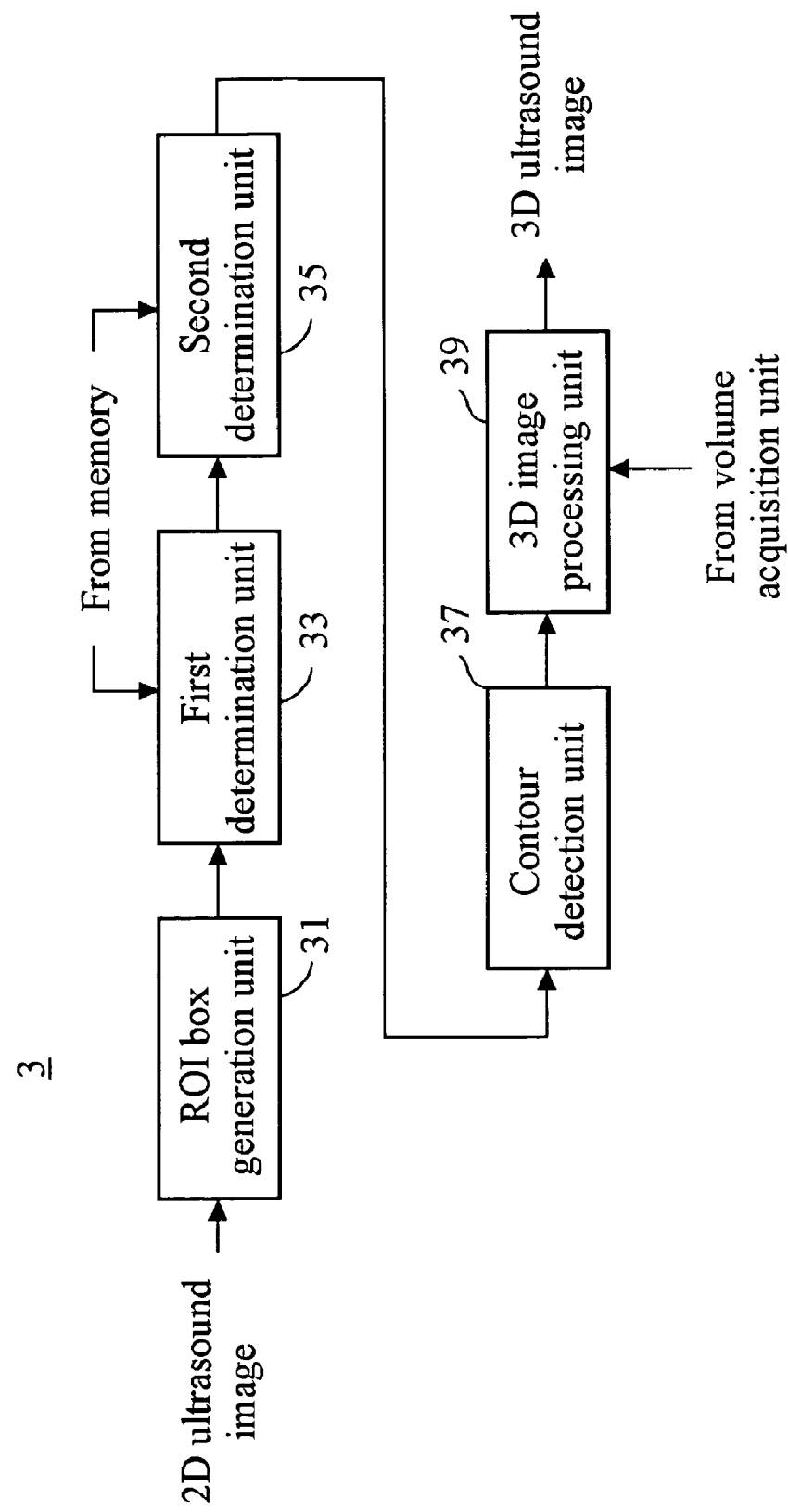

| | 46 | | | 48 | |
|---|---|---|---|---|---|
| 42 | -1 | -1 | -1 | -1 | -1 |
| | 0 | 0 | 0 | 0 | 0 |
| | 0 | 0 | 0 | 0 | 0 |
| | 0 | 0 | 0 | 0 | 0 |
| 44 | 1 | 1 | 1 | 1 | 1 |

APPARATUS AND METHOD FOR FORMING 3D ULTRASOUND IMAGE

FIELD OF THE INVENTION

The present invention generally relates to a 3-dimensional (3D) ultrasound diagnostic system, and more particularly to an apparatus and a method for automatically detecting a contour from a 2-dimensional (2D) ultrasound image of a target object and forming a 3D ultrasound image with volume data within the contour.

BACKGROUND OF THE INVENTION

A 3-dimensional (3D) ultrasound diagnostic system is a medical equipment for providing clinical information such as spatial information, anatomical information and the like, which cannot be provided from a conventional 2-dimensional image. The 3D ultrasound diagnostic system acquires volume data from signals received from a target object through a probe, and performs a scan conversion process for the acquired volume data. A 3D ultrasound image of the target object is displayed on a display device such as a monitor, a screen or the like by performing a rendering process upon images obtained from the scan-converted data. This is so that a user can obtain clinical information of the target object.

As is well-known in the art, the probe typically has a plurality of transducers, wherein the respective timing of inputting pulse signals to each transducer is appropriately delayed. This is so that a focal ultrasound beam is transmitted into the target object along a transmit scan line. Each transducer receives echo signals reflected from a focal point on the transmit scan line in a different reception time and converts the echo signal to reception signals of an electrical signal. The reception signals are transmitted to a beam former. The reception signals are appropriately delayed, wherein the delayed reception signals are summed in the beam former. This is so that the reception focal beam representing an energy level reflected from the focal point on the transmit scan line is outputted. Until a 2D slice image of the target object formed by the reception focal beams for a plurality of scan lines is generated, the above process is repeatedly carried out.

A volume data acquisition unit outputs the volume data by synthesizing 2D ultrasound images, which represent sectional planes of the target object, inputted from the beam former. The volume data are generated from signals reflected from the target object existing in a 3D space and defined in torus coordinates. Therefore, in order to perform a rendering process for the volume data in a display device having Cartesian coordinates (e.g., monitor, screen and the like), the scan conversion for performing coordinate conversion of the volume data is required. The scan conversion is implemented in a scan converter.

Scan-converted volume data in the scan converter are rendered through a typical volume rendering process so that the 3D ultrasound image is displayed. The user obtains clinical information of the target object through the 3D ultrasound image displayed on the display device.

The 3D ultrasound diagnostic system is primarily utilized for displaying a shape of a fetus with the 3D ultrasound image in the fields of obstetrics and gynecology. After acquiring volume data by scanning an abdominal region of a pregnant woman, the volume rendering process is performed upon the acquired volume data. This is so that the shape of the fetus can be displayed with the 3D ultrasound image. However, since the volume data includes mixed data of uterus tissue, adipose tissue, amniotic fluid, floating matters and the fetus, if the rendering process is directly applied to the volume data, it is difficult to clearly display the shape of the fetus with the 3D ultrasound image. Therefore, in order to display the shape of the fetus with the 3D ultrasound image, it is required to segment the fetus region from neighboring regions such as the amniotic fluid and the like.

Accordingly, through the use of external interface devices (e.g., a mouse, a keyboard and the like) connected to the 3D ultrasound diagnostic system, a region of interest (ROI) box enclosing the shape of a fetus in a 2D ultrasound image, which is displayed on the display device, can be generated as illustrated in FIG. 1A. Thereafter, a final ROI box is generated by finely operating the external interfaces as illustrated in FIG. 1B. The volume data existing in a contour detected from an image in the ROI box are rendered such that the 3D ultrasound image of the fetus can be displayed.

However, since the generation of ROI box generation and the detection of contour for the target object image are manually operated by the user in the 3D ultrasound diagnostic system, the quality of the finally displayed 3D ultrasound image depends on the expertise of the user. That is, the size of the ROI box is not consistent according to the user generating the ROI box. As such, there is often a problem since a desired 3D ultrasound image of the target object cannot be accurately displayed.

Also, even if the user is an expert, there is a problem in that it takes a long working time to generate the ROI box and detect the contour of the target object image from the 2D ultrasound image. This is because the user generates the ROI box directly on the 2D ultrasound image. Moreover, if the size of the ROI box is not accurate for the desired 3D ultrasound image of the target object, then there is a problem in that an error may be generated in the volume data rendering process or the contour detection process of the target object in the ROI box.

SUMMARY OF THE INVENTION

Therefore, it is an objective of the present invention to provide an apparatus and a method for forming an accurate 3D ultrasound image of a target object while reducing errors, which may be generated in a rendering process of a volume data and a contour detection process of the target object. It is a further objective of the present invention to reduce the time consumed in the process of generating a region of interest (ROI) box and the process of detecting contour of the target object by automatically generating the ROI box and detecting the contour of the target object existing in the ROI box.

In accordance with an aspect of the present invention, there is provided an apparatus for forming a 3-dimensional (3D) ultrasound image, comprising: a first unit for generating a region of interest (ROI) box on a 2D ultrasound image; a second unit for detecting contour of a target object in the ROI box; and a third unit for forming a 3D ultrasound image by rendering volume data existing in the detected contour.

In accordance with another aspect of the present invention, there is provided a method for forming a 3-dimensional (3D) ultrasound image, comprising the steps of: a) generating a region of interest (ROI) box on a 2D ultrasound image; b) detecting contour of a target object in the ROI box; and c) forming a 3D ultrasound image by rendering volume data existing in the detected contour.

BRIEF DESCRIPTION OF THE DRAWINGS

The above and other objects and features of the present invention will become apparent from the following description of preferred embodiments given in conjunction with the accompanying drawings, in which:

FIG. 2 is a schematic block diagram illustrating a device for forming a 3D ultrasound image, which is constructed in accordance with the preferred embodiment of the invention;

DETAILED DESCRIPTION OF THE PRESENT INVENTION

Figure 1A:
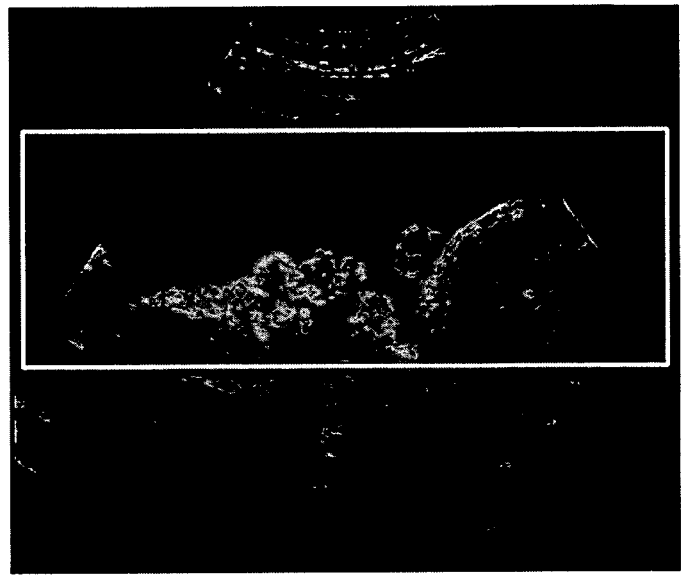
FIGS. 1A and 1B are diagrams depicting region of interest (ROI) boxes generated on 2D ultrasound images.
Figure 1B:
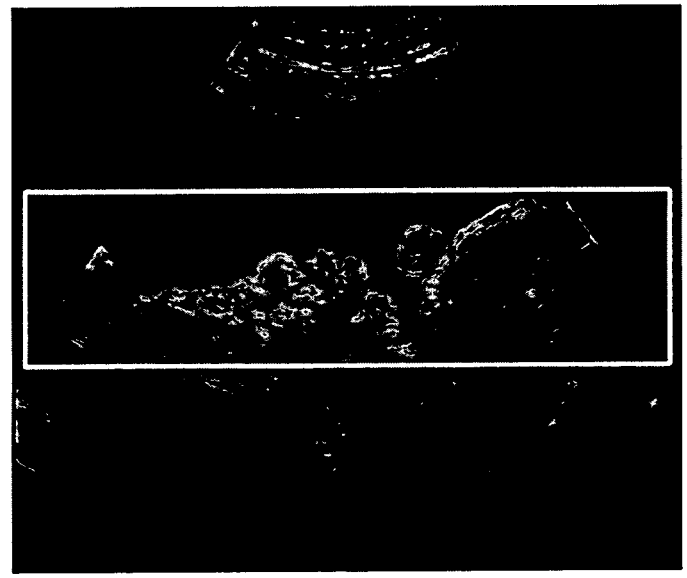

FIG. 2 is a schematic block diagram showing a 3-dimensional (3D) ultrasound image forming device 3 in a 3D ultrasound diagnostic device constructed in accordance with the preferred embodiment of the invention. The 3D ultrasound image forming device 3 includes a region of interest (ROI) box generation unit 31, a first determination unit 33, a second determination unit 35, a contour detection unit 37 and a 3D image processing unit 39. As the 3D key of a control panel (not shown) mounted in the 3D ultrasound image forming device 3 is activated, the 3D ultrasound image forming device 3 starts to operate.

If a user activates the 3D key, then one of the 2D ultrasound images, which are acquired through a probe and a beam former in the 3D ultrasound diagnostic system, is displayed with a brightness mode (B-mode) on a display device (not shown). In accordance with the present invention, the 2D ultrasound image displayed on the display device is a 2D ultrasound image representing a central slice of the target object. The B-mode represents that energies of signals reflected from the target object are displayed with a brightness level. The ROI box generation unit 31 automatically generates the ROI box on the 2D ultrasound image displayed on the display device.

The first determination unit 33 determines whether the size of the ROI box, which is automatically generated, is suitable for that of the 2D ultrasound image of the target object. The second determination unit 35 determines whether the contour of the target object, which exists in the ROI box, can be detected. The contour detection unit 37 detects the contour of the target object existing in the ROI box. The 3D image processing unit 39 selects the volume data, which exist in the contour of the target object, among volume data stored in a volume data acquisition unit and forms a 3D ultrasound image by rendering them.

Hereinafter, the ROI box generation unit 31 for automatically generating the ROI box on the 2D ultrasound image, which is displayed on the display device of the 3D ultrasound diagnostic system, will be described in detail by referring to FIGS. 3 to 5F.

Figure 3:
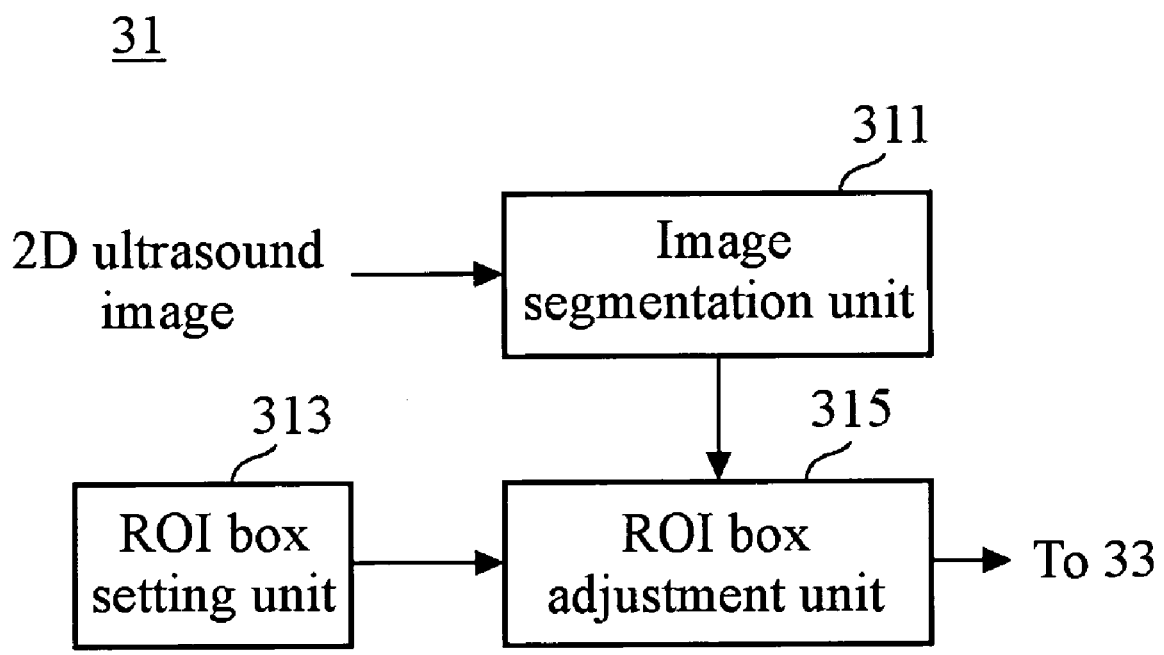
FIG. 3 is a detailed block diagram illustrating a ROI box generation unit of FIG. 2.

FIG. 3 is a detailed block diagram showing the ROI box generation unit 31 of FIG. 2. As shown in FIG. 3, the ROI box generation unit 31 includes an image segmentation unit 311, a ROI box setting unit 313 and a ROI box adjustment unit 315. The image segmentation unit 311 segments the 2D ultrasound image into a target object image and a background image neighbored with the target object. The ROI box setting unit 313 sets a ROI box having a predetermined size on the 2D ultrasound image, while the ROI box adjustment unit 315 adjusts the size of the ROI box.

Since some factors, which make it difficult to clearly display the 3D ultrasound image (e.g. a speckle noise and the like), exist in the 2D ultrasound image for forming the volume data of the target object, a process for removing such factors should be first carried out. The image processing unit 311 removes the speckle noise existing in the 2D ultrasound image through a filtering process. The filtering process is carried out by using a Lee filter in order to remove only the speckle noise, while preserving edge information of the target object within the 2D ultrasound image, in accordance with the preferred embodiment of the present invention.

The image segmentation unit 311 sets a threshold value for binarization of the 2D ultrasound image in which the speckle noise has been removed. The 2D ultrasound image is binarized by referring to the threshold value so that the 2D ultrasound image can be segmented into two classes. Since the 2D ultrasound image is displayed with the B-mode, the threshold value is set according to the brightness of the 2D ultrasound image. For example, if the threshold value of the 2D ultrasound image having pixel values of 0 to 255 is 't', the 2D ultrasound image is segmented into a first class having pixel values of $\{0, 1, 2, \ldots, t\}$ and a second class having pixel values of $\{t, t+1, t+2, \ldots, 255\}$.

The image segmentation unit 311 performs a first segmentation process for the 2D ultrasound image based on a first binarization threshold value t1. This is so that the 2D ultrasound image can be segmented into a target object image and a background image. A second segmentation process for the background image, which is segmented through the first segmentation process, is performed by referring to a second threshold value t2. This is so that the background image can be segmented into a target object image and a background image. Thereafter, a third segmentation process for the background image, which is segmented through the second segmentation process, is performed by referring to a third threshold value t3 so that the background image is finally segmented into a target object image and a background image. As these segmentation processes are repeatedly performed, the image segmentation unit 311 more clearly segments the 2D ultrasound image into the target object image and the background image neighboring the target object image. The resulting values segmenting the image in the image segmentation unit 311 are outputted to the ROI box adjustment unit 315.

Figure 4A:
FIGS. 4A to 4C represent examples of showing the results of performing image segmentation for a 2D ultrasound image.
Figure 4B:
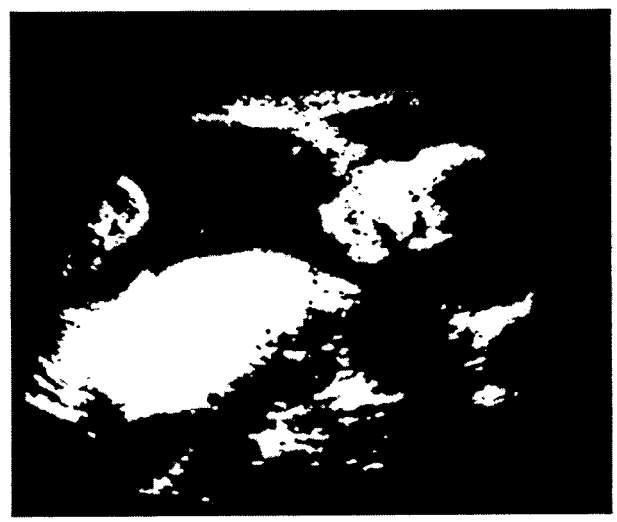
Figure 4C:
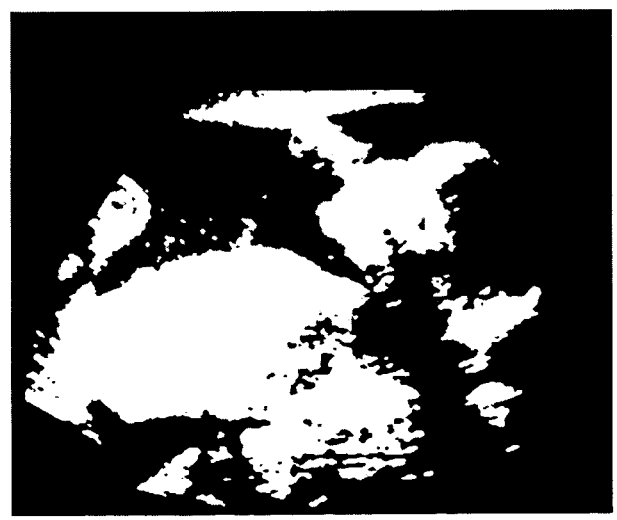

FIG. 4A shows an original 2D ultrasound image. FIG. 4B shows a 2D ultrasound image in which the image segmentation process is performed once. FIG. 4C shows a 2D ultrasound image in which the image segmentation process is performed twenty times.

The ROI box setting unit 313 sets the size of the ROI box configured with four bounds generated on the 2D ultrasound image originally displayed on the display device and outputs the set ROI box to the ROI box adjustment unit 315. Generally, the size of the ROI box is previously set according to the types of target objects to be displayed with the 3D ultrasound image.

The ROI box adjustment unit 315 adjusts the size of the ROI box set by the ROI box setting unit 313 so as to be suitable for the size of the target object image exiting in the ROI box. During this time, the characteristic of the target object image becomes an important factor for adjusting the size of the ROI box. A fetus is an example of the target object. A fetus ultrasound image has a valley at the boundary between a head and a body, wherein a front surface of the head, which is a surface of a face, has more curvedness than that of the body. Also, a characteristic exists in which the face is longer than the body.

Referring to FIGS. 5A to 5F, there will be described an example which automatically adjusts the size of the ROI box for the overall fetus to the size of the ROI box for the face in the ROI box adjustment unit 315.

Figure 5A:
FIGS. 5A to 5F show a process for automatically adjusting a size of the ROI box for a fetal face image.
Figure 5B:

First, as shown in FIG. 4C, the ROI box adjustment unit 315 selects an image existing in the ROI box set by the ROI box setting unit 313 from the image-segmented 2D ultrasound image. As shown in FIG. 5A, a binarization threshold value is set for the selected fetal image, wherein a binarization process is applied to the selected fetal image by referring to the threshold value. Next, the ROI box adjustment unit 315 removes the noise regions from the binarization regions of the fetal image. This is so that the binarization regions, which are determined with a portion of the fetal image, are detected as shown in FIG. 5B. More specifically, the ROI box adjustment unit 315 examines the brightness for each binarization region and calculates the mean of the brightness. When the brightness of the binarization regions is lower than the mean of the brightness, the binarization region is considered as a noise region and thereby removed. Also, even if the brightness is greater than the mean of the brightness, the noise regions may exist. Therefore, the ROI box adjustment unit 315 sets a threshold value at the binarization region. As such, when a pixel value of the binarization region is lower than the threshold value, the binarization region is considered as a noise region and thereby removed.

Figure 5C:
Figure 5D:
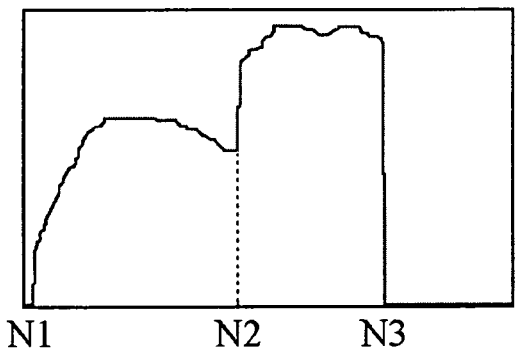

After the noise regions are removed from the binarization regions, the ROI box adjustment unit 315 assigns a pixel value of "255" to the overall pixels existing from pixels positioned at a top surface of the detected binarization region to pixels positioned at a bottom bound of the ROI box set by the ROI box setting unit 313. This is so that a binarization image of the fetus can be generated as shown in FIG. 5C. Next, the ROI box adjustment unit 315 generates a surface curved line on the binarization image as illustrated in FIG. 5D. Then, the ROI box adjustment unit 315 searches relative maximum points and relative minimum points among pixels neighboring each other at the surface curved line and appoints the relative minimum point corresponding to the valley between the head and the body of the fetus.

As shown in FIG. 5D, after the relative minimum point corresponding to the valley between the head and the body of the fetus is appointed as N2, the ROI box adjustment unit 315 appoints a starting point N1 and an ending point N3 of the surface curved line. This is so that the surface curved line is segmented into two areas of [N1, N2] and [N2, N3]. The ROI box adjustment unit 315 calculates the number of the relative maximum points existing at a first surface curved line area of [N1, N2] and a second surface curved line area of [N2, N3]. Further, an area having a greater number of relative maximum points is determined as the face surface of the fetus. Since the curvedness of the surface of the fetal face is greater than that of the fetal body, the number of relative maximum points at the fetal face is greater than that of the fetal body.

Figure 5E:
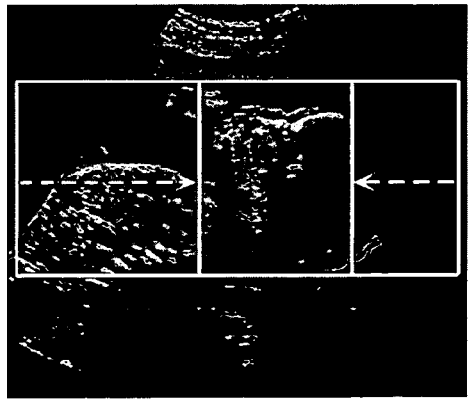

After the face area of the fetus is determined, the ROI box adjustment unit 315 moves the left bound of the ROI box to the relative minimum point N2 of the surface curved line. It further moves the right bound of the ROI box to the right bound of the surface curved line. Therefore, the ROI box adjustment unit 315 automatically adjusts the positions of left/right bounds of the ROI box set by the ROI box setting unit 313 so as to be suitable for a face size of the fetal image. FIG. 5E shows an example wherein the left/right bounds of the ROI box set on the 2D ultrasound image displayed on the display device are automatically adjusted by the ROI box adjustment unit 315.

After adjusting the left/right bounds of the ROI box for the fetal face image, the ROI box adjustment unit 315 performs the binarization, noise region removal, binarization image generation and surface curved line generation processes for the fetal face image existing in the adjusted ROI box. In order to generate a binarization image from the fetal image, the ROI box adjustment unit 315 assigns a pixel value of "255" to the overall pixels existing from the left most surface of the binarization regions detected from the fetal face image to the right bound of the adjusted ROI box.

Figure 5F:
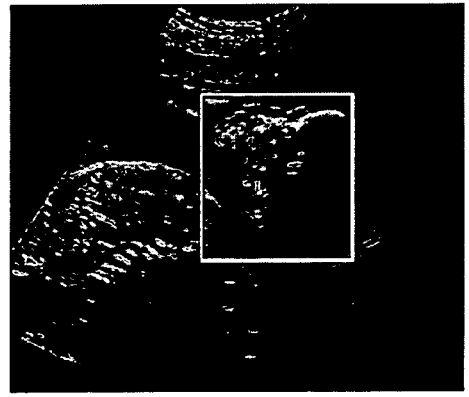

The ROI box adjustment unit 315 moves the top bound of the ROI box toward the bottom bound of the ROI box until the top bound meets with the surface curved line. It then determines the position, which the top bound is met with the surface curved line, as the top bound position of the ROI box. Also, the ROI box adjustment unit 315 moves the bottom bound of the ROI box toward the top bound of the ROI box until the bottom bound reaches the surface curved line. It then determines the position, which the bottom bound of the ROI box is met with the surface curved line, as the bottom bound position of the ROI box. FIG. 5F shows an example wherein the ROI box set on the 2D ultrasound image is finally adjusted for the fetal face image by the ROI box adjustment unit 315.

For the sake of convenience, while the ROI box generation process in the ROI box generation unit 31 is described for the fetal image (which is an example), it will be apparent that the size of a ROI box set on an arbitrary target object of a 2D ultrasound image can be adjusted to be suitable for the size of the arbitrary target object by automatically adjusting the bounds of the ROI box according to the above ROI box generation process.

The first determination unit 33 illustrated in FIG. 2 determines the suitability of the size of ROI box for the target object image generated in the ROI box generation unit 31. Generally, the ROI box generated from the ROI box generation unit 31 has a similar size for the same type of target object image. Accordingly, the first determination unit 33 selects one of the standard histograms, which are previously set for each type of target object images, from a memory (not shown) built in the 3D ultrasound diagnostic system. Then, a mean square error value of the selected histogram and histograms for the target object image, which exists in the ROI box inputted from the ROI box generation unit 31, is calculated.

As a result, if the calculated mean square error value is greater than the previously predetermined value, the first determination unit 33 determines that the size of the ROI box generated from the ROI box generation unit 31 is not suitable and then stops the operation of the 3D ultrasound diagnostic system. Thereafter, it notifies that the size of the generated ROI box is not suitable to the user. On the other hand, if the calculated mean square error value is less than the predetermined value, the first determination unit 33 determines that the size of the ROI box generated from the ROI box generation unit 31 is suitable. It then outputs the 2D ultrasound image inputted from the ROI box generation unit 31 to the second determination unit 35. The histogram for the target object image in the ROI box, which is inputted from the ROI box generation unit 31, is transmitted to the memory so as to renew the standard histogram of the target object image.

The second determination unit 35 shown in FIG. 2 determines whether the contour of the target object image in the ROI box can be detected. That is, as the second determination unit 35 determines the capability of the contour detection of the target object image in the ROI box, it improves the efficiency for displaying the 3D ultrasound image in the 3D ultrasound diagnostic system. Since the absorption and reflection of the ultrasound are different according to each part of the target object (e.g., the fetus and the amniotic fluid enclosing the fetus), boundaries are formed in the target object of the 2D ultrasound image due to an edge effect clearly representing the differences in brightness. The second determination unit 35 determines the capability of the contour detection for the target object on the basis of the edge effect.

Figures 6A, 6B:
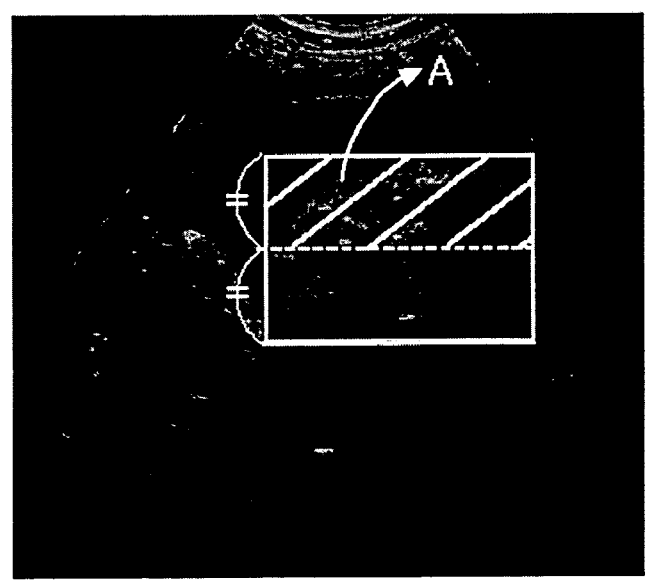
FIG. 6A illustrates a mask used for determining the capability of the contour detection for the target object image.
FIG. 6B is a diagram showing a 2D ultrasound image applying the mask.

FIG. 6A shows a mask used for determining whether the contour of the 2D ultrasound image can be detected. FIG. 6B shows a 2D ultrasound image applying the mask of FIG. 6A. A mask configured with pixels of 3×3 is commonly used so as to detect the boundaries of the target object in the 2D ultrasound image. In designing the mask for the 2D ultrasound image, (1) a pixel value corresponding to a dark portion is set with "−1", (2) a pixel value corresponding to a bright portion is set with "1", and (3) a pixel value forming the boundary between the dark portion and the bright portion is set with "0". In accordance with the preferred embodiment of the present invention, a mask configured with pixels of 5×5 expanding a pixel region forming the boundary is used as shown in FIG. 6A. The size of the pixel configuring the mask is identical to that of the pixel configuring the 2D ultrasound image.

The second determination unit 35 detects pixels forming the boundary by matching a pixel positioned at a center of the mask (illustrated in FIG. 6A) with all pixels existing in a region "A" corresponding to a portion from the top bound of the ROI box to half of the fetal face image one-to-one. The reason why the detection process of pixels forming the boundary is carried out only for such portion (from the top bound of the ROI box to half of the fetal face image) is to improve the detection speed and to prevent the edge region from being generated at undesired regions.

More specifically, the central pixel of the mask of 5×5 is first matched with an arbitrary pixel existing in the region "A". Next, the second determination 35 selects the pixels in the region "A", which are distributed adjacent to the arbitrary pixel and matched with the pixels configuring the mask of 5×5 one to one. Thereafter, the second determination unit 35 multiplies the pixel values of the selected pixels by one pixel value of pixels configuring the mask of 5×5, i.e., "−1", "1" or "0", respectively. It then sums up the resulting values so that the second determination unit 35 finally determines the summed value as a new pixel value for the arbitrary pixel, which exits in the region "A" and is matched with the central pixel of the mask of 5×5. The second determination unit 35 applies the above process to all the pixels existing in the region "A" and determines pixels forming the boundary of the target object with pixels having over a predetermined pixel value among the newly determined pixel values. In accordance with the preferred embodiment of the present invention, pixels corresponding to 20% of a high rank among the newly determined pixel values are determined as reference pixels representing the edge pixels.

After the pixels forming the boundary are detected, the second determination unit 35 calculates a ratio of the number of the boundary pixels to all the number of pixels configuring the region "A" and variance of pixels forming the boundary. Thereafter, the ratio and the variance are applied to the following equation 1 so that the second determination unit 35 determines the capability of the contour detection of the target object.

$$D_i = \alpha R_{1i} + \beta R_{2i} \qquad \text{Eq. 1}$$

Wherein, i is the number of 2D ultrasound images for the same types of target object inputted to the second determination unit 35, $D_i$ is a determination numerical value representing the capability of the contour detection, $R_{1i}$ is a ratio of the number of the boundary pixels to all the number of pixels configuring the region "A", and $R_{2i}$ is a variance of pixels forming the boundary. $\alpha$ and $\beta$, which are coefficients of an equation such as equation 1, are obtained through a contour detection experiment of various 2D ultrasound images for the same type of target object.

In particular, the second determination unit 35 selects various 2D ultrasound images for the same type of target object from the memory built in the 3D ultrasound diagnostic system. The second determination unit 35 gives a determination value "1" to 2D ultrasound images whose contour can be detected. It further gives a determination value "0" to 2D ultrasound images whose contour cannot be detected among the selected 2D ultrasound images. The second determination unit 35 calculates $\alpha$ and $\beta$ when the mean square error value, which is defined in the following equation 2, is minimized by using the determination values of each 2D ultrasound image selected from the memory, as well as the ratios $R_{1i}$ and $R_{2i}$.

$$\in = \sum_i (D_i - (\alpha R_{1i} + \beta R_{2i}))^2 \qquad \text{Eq. 2}$$

In order to minimize the mean square error value, the second determination unit 35 performs the partial differentiation for equation 2 for $\alpha$ and $\beta$. In case the resulting values of the equation performing the partial differentiation become "0", the $\alpha$ and $\beta$ are determined as the coefficients of equation 1. The second determination unit 35 applies the $R_{1i}$, $R_{2i}$, $\alpha$ and $\beta$ to equation 1 so that the determination values of the target object image in the ROI box, which are inputted through the first determination unit 33, can be calculated. Finally, the second determination unit 35 determines that the contour of the target object image in the ROI box can be detected when the calculated determination value is greater than a predetermined set value. Then, the inputted 2D ultrasound image is outputted to the contour detection unit 37 (illustrated in FIG. 2). On the other hand, when the calculated determination value is less than the predetermined set value, the second determination unit 35 determines that it is impossible to detect the contour of the target object image in the ROI box and stops the operation of the 3D ultrasound diagnostic system. Thereafter, the second determination unit 35 notifies that it is impossible to detect the contour of the target object image to the user.

For the sake of convenience, a process for determining the capability of the contour detection for the top surface of the fetal face image by detecting the boundary pixels existing between the top bound of the ROI box and the fetal face image is described. However, boundary pixels existing between the bottom, left and right bounds of the ROI box and the fetal face image should be detected in order to determine the capability of the contour detection of fetal face image according to the above process. For such process, masks transforming the pixel values of the mask of 5×5 of FIG. 6A should be used. That is, for the bottom bound of the ROI box, a mask should be used in which the pixel values positioned at the first row 42 of the mask of 5×5 (illustrated in FIG. 6A) are "−1" and the pixel values positioned at the fifth row 44 are "1". For the left bound of the ROI box, a mask should be used in which the pixel values positioned at the first column 46 of the mask of 5×5 (illustrated in FIG. 6A) are "−1" and the pixel values positioned at the fifth column 48 are "1". Also, for the right bound of the ROI box, a mask should be used in which the pixel values positioned at the first column 46 of the mask of 5×5 (illustrated in FIG. 6A) are "1" and the pixel values positioned at the fifth column 48 are "−1".

Since the processes for determining the capability of the contour detection for the bottom, left and right surfaces of the fetal face image are performed upon the above process, a detailed description will be omitted herein. Also, it is apparent that the determination process for determining the capability of the contour detection, which is described above, can be applied to an arbitrary target object.

The contour detection unit 37 (illustrated in FIG. 2) detects the contour of the target object image exiting in the ROI box, which is inputted from the second determination unit 35. First, in order to compensate the deficiency of the target object not having a sufficient brightness contrast, the contour detection unit 37 performs the smoothing of the target object by removing the speckle noise existing in the target object in the ROI box through the use of the Lee filter or the like. Thereafter, brightness contrast stretching for the target object is carried out by providing pixel values, which are defined in equation 3, to the pixels configuring the target object image in the ROI box.

$$F(x) = \begin{cases} 0 & \text{for} \quad x \leq \text{low} \\ \frac{255 \times (x - \text{low})}{(\text{high} - \text{low})} & \text{for} \quad \text{low} < x < \text{high} \\ 255 & \text{for} \quad \text{high} \leq x \end{cases} \quad \text{Eq. 3}$$

Wherein, F(x) is a new pixel value provided by the contour detection unit 37, x is an old pixel value of the pixel configuring the target object image inputted from the second determination unit 35, 'low' is a critical value in a low range of the histogram for the target object inputted from the second determination unit 35, and 'high' is a critical value in a high range of the histogram for the target object inputted from the second determination unit 35.

Figure 7A:
FIGS. 7A and 7B show examples of performing smoothing and brightness contrast for the target object image in the ROI box.
Figure 7B:
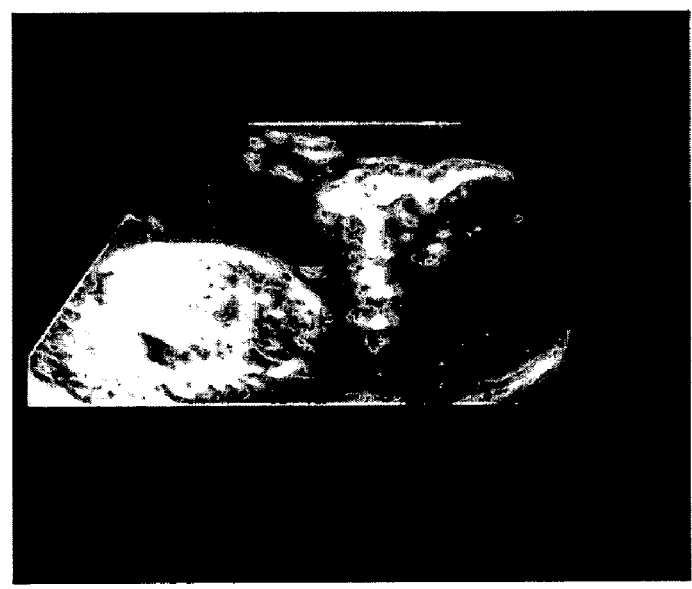

FIGS. 7A and 7B represent examples showing the results of performing the smoothing and brightness contrast stretching for the target object in the ROI box, which is previously set, in the contour detection unit 37. Hereinafter, a process for detecting the contour of the fetal image will be described.

Figure 8A:
FIGS. 8A and 8B show examples of performing binarization for the target object image in the ROI box.
Figure 8B:

The contour detection unit 37 sets a binarization threshold value for the fetal image in the ROI box and performs the binarization for the fetal image by the set binarization threshold value as a reference. Next, the contour detection unit 37 detects regions, which are determined as a portion of the fetal image, by removing the noise regions from the binarization regions of the fetal image. That is, the contour detection unit 37 examines the brightness values for the binarization regions and calculates the mean thereof. In the binarization regions, if the brightness value of the binarization region is less than the mean brightness value, the binarization region is considered as a noise region and thereby removed. Also, even if the brightness value is greater than the mean brightness value, since the noise region may exist, the contour detection unit 37 sets a threshold value for the size of the binarization region. Therefore, if the size of the binarization region is less than the threshold value, the binarization region is considered as a noise region and thereby removed. FIGS. 8A and 8B represent examples showing the results of performing the binarization for the fetal image in the ROI box and removing the noise regions from the binarization regions in the contour detection unit 37.

Figure 9A:
FIGS. 9A and 9B show examples of detecting contour at a top surface of a fetal image.
Figure 9B:
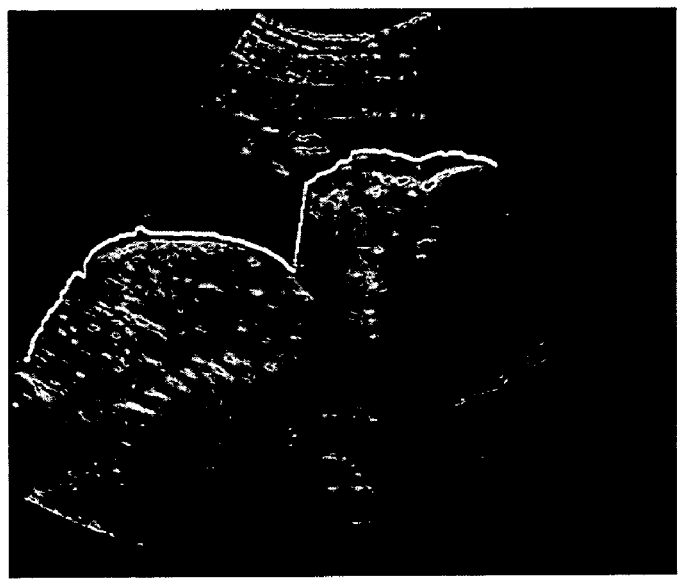

Hereinafter, a contour detection process performed in the detection unit 37 will be described in view of FIG. 9. If the binarization regions for the fetal image are generated as shown in FIG. 8B, the contour detection unit 37 moves the top bound (not shown) of the ROI box toward the bottom bound (not shown) in order to detect the contour of the fetal image. Next, the contour detection unit 37 extracts pixels corresponding to top surfaces of the binarization regions, which met with the top bound of the ROI box, and connects the extracted pixels with the pixels neighboring each other. Since a deep valley between the head and the body of the fetal image exists, the contour for the top surfaces of the fetal image are obtained as illustrated in FIG. 9A. If the separated contours as illustrated in FIG. 9A are detected, the contour detection unit 37 connects the contours to thereby obtain a final contour. An example, which applies the detected contour to the 2D ultrasound image displayed on the display device, is illustrated in FIG. 9B.

For the sake of convenience, the contour detection process for only the top surface of the fetal image is described. Also, the contour detection for the bottom, left and right surfaces can be detected by applying the above process to the bottom, left and right bounds. Finally, the contour detection unit 37 outputs the 2D ultrasound image in which the contour detected from the fetal image is displayed to the 3D image processing unit 39 (illustrated in FIG. 2).

The 3D image processing unit 39 forms the 3D ultrasound image by rendering volume data only for the target object. For such process, the 3D image processing unit 39 selects the volume data corresponding to the target object, which is enclosed by the contour, inputted from the contour detection unit 37 from the voltage data stored in the voltage data acquisition unit (not shown). Next, the 3D image processing unit 39 performs the scan conversion for the selected volume data and then a typical volume rendering process is applied so that the 3D ultrasound image can be more accurately displayed.

As described above, since the ROI box is automatically generated and the contour of the target object image existing in the ROT box is automatically detected, the time consumption for the ROI box generation and the contour detection of the target object image can be reduced. Also, as the suitability of the size of the automatically generated ROT box and the capability of the contour detection from the target object image in the ROT box are determined, errors generated from the volume data rendering and the contour detection of the target object image can be reduced. As such, a more accurate 3D ultrasound image for the target object can be provided to the user of the 3D ultrasound diagnostic system.

While the present invention has been described and illustrated with respect to a preferred embodiment of the invention, it will be apparent to those skilled in the art that variations and modifications are possible without deviating from the broad principles and teachings of the present invention which should be limited solely by the scope of the claims appended hereto.

What is claimed is:

1. An apparatus for forming a 3-dimensional (3D) ultrasound image, comprising:
   a generation unit configured to generate a binarization image of a 2D ultrasound image to generate a surface curved line of a target object on the 2D ultrasound image and automatically generate a region of interest (ROI) box for the target object on the 2D ultrasound image by moving bounds of the ROI box to pixels closest to the surface curved line;
   a first determination unit configured to calculate a mean square error value between a predetermined standard histogram for a 2D ultrasound image of the target object and a histogram for a 2D ultrasound image within the ROI box, and determine whether the ROI box is suitably generated for a display of the target object therewithin based on the calculation result;
   a detection unit configured to detect a contour of the target object in the ROI box; and
   a formation unit configured to form the 3D ultrasound image by rendering volume data existing in the detected contour.

2. The apparatus as recited in claim 1, further comprising:
   a second determination unit configured to determine whether the contour of the 2D ultrasound image of the target object is detectable.

3. The apparatus as recited in claim 1, wherein the generation unit comprises:
   a first unit configured to segment the 2D ultrasound image into an image of the target object and an image of a background;
   a second unit configured to set the ROI box with a predetermined size according to types of the target object on the 2D ultrasound image; and
   a third unit configured to adjust a size of the ROI box to be suitable for a size of the target object.

4. The apparatus as recited in claim 3, wherein the third unit is configured to perform the following functions:
   removing a noise region in a binarization region of the image of the target object, after performing binarization for the image of the target object in the ROI box;
   generating the binarization image for the target object by providing predetermined pixel values to the binarization region and the surface curved line of the binarization image; and
   adjusting the bounds of the ROI box by moving each bound to the pixels closest to the surface curved line.

5. The apparatus as recited in claim 2, wherein the second determination unit is configured to perform the following functions:
   extracting pixels forming a boundary of the target object by matching pixels of a mask of a predetermined type with pixels of the image of the target object in the ROI box one-to-one; and
   determining a capability of contour detection of the target object by calculating a ratio of the number of boundary pixels to the number of all pixels matched with the mask one-to-one and a variance of pixels forming the boundary according to the following equation:

$$D_i = \alpha R_{1i} + \beta R_{2i}$$

where i is the number of a 2D ultrasound image of a same type of target object and previously stored in a memory, $D_i$ is a determination numerical value representing the capability of the contour detection, $R_{1i}$ is a ratio of the number of the boundary pixels to the number of all pixels matched with the mask one-to-one, and $R_{2i}$ is the variance of the pixels forming the boundary, and where $\alpha$ and $\beta$, which are coefficients obtained through a contour detection experiment of various 2D ultrasound images for the same type of target objects as the target object, are the values where a mean square error value defined in the following equation is minimized:

$$\epsilon = \sum_i (D_i - (\alpha R_{1i} + \beta R_{2i}))^2$$

where, to minimize the mean square error value, a partial differentiation of the mean square error value is performed for each $\alpha$ and $\beta$, and where the $\alpha$ and $\beta$ are determined as the coefficients when resulting values of the partial differentiation are zero.

6. The apparatus as recited in claim 1, wherein the detection unit is configured to perform the following functions:
   performing a brightness contrast stretching for the image of the target object for sufficient brightness contrast of the target object in the ROI box;
   removing a noise region from a binarization region of the target object, after performing binarization of the target object in the ROI box;
   extracting pixels existing in a surface of the binarization region which meets the bounds of the ROI box by adjusting the bounds of the ROI box; and
   detecting the contour of the target object by connecting the extracted pixels.

7. A method for forming a 3-dimensional (3D) ultrasound image, comprising:
   a) generating a binarization image of a 2D ultrasound image to generate a surface curved line of a target object on the 2D ultrasound image and automatically generating a region of interest (ROI) box for the target object on the 2D ultrasound image by moving bounds of the ROI box to pixels closest to the surface curved line;
   b) calculating a mean square error value of a predetermined standard histogram for a 2D ultrasound image of the target object and a histogram for a 2D ultrasound image within the ROI box, and determining whether the ROI box is suitably generated for a display of the target object therewith based on the calculation result;
   c) detecting a contour of the target object in the ROI box; and
   d) forming the 3D ultrasound image by rendering volume data existing in the detected contour.

8. The method as recited in claim 7, further comprising:
   e) determining whether the contour of the 2D ultrasound image of the target object is detectable.

9. The method as recited in claim 7, wherein a) further comprises:
   a1) segmenting the 2D ultrasound image into an image of the target object and an image of a background neighboring the target object;
   a2) setting a ROI box with a predetermined size on the 2D ultrasound image; and
   a3) adjusting the size of the ROI box to be suitable for a size of the 2D ultrasound image of the target object.

10. The method as recited in claim 9, wherein a3) further comprises:
    a3-1) removing a noise region in a binarization region of the image of the target object, after performing binarization for the image of the target object in the ROI box;

a3-2) generating the binarization image for the target object by providing predetermined pixel values to the binarization region and the surface curved line of the binarization image; and a3-3) adjusting the bounds of the ROI box by moving each bound to the pixels closest to the surface curved line.

11. The method as recited in claim 8, wherein e) further comprises:

e1) extracting pixels forming a boundary of the target object by matching pixels of a mask of a predetermined type with pixels of the image of the target object in the ROI box one-to-one; and e2) determining a capability of contour detection of the target object by calculating a ratio of the number of boundary pixels to the number of all pixels matched with the mask one-to-one and a variance of pixels forming the boundary according to the following equation:

$$D_i = \alpha R_{1i} + \beta R_{2i}$$

where i is the number of a 2D ultrasound image of a same type of target object and previously stored in a memory, $D_i$ is a determination numerical value representing the capability of the contour detection, $R_{1i}$ is a ratio of the number of the boundary pixels to the number of all pixels matched with the mask one-to-one, and $R_{2i}$ is the variance of the pixels forming the boundary, and where $\alpha$ and $\beta$, which are coefficients obtained through a contour detection experiment of various 2D ultrasound images for the same type of target objects as the target object, are the values where a mean square error value defined in the following equation is minimized:

$$\in = \sum_i (D_i - (\alpha R_{1i} + \beta R_{2i}))^2$$

where, to minimize the mean square error value, a partial differentiation of the mean square error value is performed for each $\alpha$ and $\beta$, and where the $\alpha$ and $\beta$ are determined as the coefficients when resulting values of the partial differentiation are zero.

12. The method as recited in claim 7, wherein b) further comprises:

b1) performing a brightness contrast stretching for the image of the target object for sufficient brightness contrast of the target object in the ROI box;

b2) removing a noise region from a binarization region of the target object, after performing binarization of the target object in the ROI box;

b3) extracting pixels existing in a surface of the binarization region which meets the bounds of the ROI box by adjusting the bounds of the ROI box; and b4) detecting the contour of the target object by connecting the extracted pixels.

* * * * *